US008417474B2

(12) United States Patent
Datta et al.

(10) Patent No.: US 8,417,474 B2
(45) Date of Patent: *Apr. 9, 2013

(54) METHODS OF USE OF SUBSTRATE HAVING PROPERTIES OF KERATINOUS TISSUE

(75) Inventors: Saswati Datta, Cincinnati, OH (US); William Randal Belcher, Bellbrook, OH (US); Sandra Lou Murawski, Fairfield, OH (US); Mannie Lee Clapp, Mason, OH (US); Steven Hardy Page, Lawrenceburg, IN (US); Magda El-Nokaly, Cincinnati, OH (US); Richard Tweddell, III, Hamilton, OH (US); Sohini Paldey, Cincinnati, OH (US); Louis Fay Wong, Mason, OH (US); Ronald R. Warner, Cincinnati, OH (US); Kerstin Ann-Margret Nolkrantz, Brussels (BE); Chitra Laxmanan, Cincinnati, OH (US); Brian Naveen Ranade, Cincinnati, OH (US); Jianjun Justin Li, West Chester, OH (US); Randall Glenn Marsh, Hamilton, OH (US); Maria Montserrat Sanchez Peña, Brussels (BE)

(73) Assignee: The Procter & Gamble Company, Cincinnati, OH (US)

( * ) Notice: Subject to any disclaimer, the term of this patent is extended or adjusted under 35 U.S.C. 154(b) by 1412 days.

This patent is subject to a terminal disclaimer.

(21) Appl. No.: 11/702,404

(22) Filed: Feb. 5, 2007

(65) Prior Publication Data
US 2007/0288186 A1 Dec. 13, 2007

Related U.S. Application Data

(60) Provisional application No. 60/772,469, filed on Feb. 10, 2006.

(51) Int. Cl.
*G01N 37/00* (2006.01)
*G06G 7/48* (2006.01)
(52) U.S. Cl. .......................................... 702/81; 703/12
(58) Field of Classification Search ........................ None
See application file for complete search history.

(56) References Cited

U.S. PATENT DOCUMENTS

| 4,032,685 | A | * | 6/1977 | Yamada | 428/399 |
|---|---|---|---|---|---|
| 4,842,893 | A | | 6/1989 | Yializis et al. | |
| 4,937,030 | A | | 6/1990 | Nishiyama | |
| 4,954,371 | A | | 9/1990 | Yializis | |
| 5,015,431 | A | | 5/1991 | Charkoudian | |
| 6,558,422 | B1 | | 5/2003 | Baker et al. | |
| 6,821,379 | B2 | | 11/2004 | Datta et al. | |
| 6,841,201 | B2 | | 1/2005 | Shanov et al. | |
| 6,904,820 | B2 | | 6/2005 | Tate | |
| 2002/0045941 | A1 | * | 4/2002 | Ishikubo et al. | 623/15.12 |
| 2002/0082692 | A1 | | 6/2002 | Van Blitterswijk | |
| 2003/0091827 | A1 | * | 5/2003 | Zamora et al. | 428/413 |
| 2004/0057924 | A1 | * | 3/2004 | Gustavsson | 424/74 |
| 2004/0131740 | A1 | * | 7/2004 | Woodhouse et al. | 426/549 |
| 2007/0128255 | A1 | | 6/2007 | Belcher et al. | |

FOREIGN PATENT DOCUMENTS

GB    2174331 A    11/1986

OTHER PUBLICATIONS

Tran et al. (Thin Solid Films 491 (2005) 123-132).*
Hamerli et al. (Surface and Coatings Technology 174-175 (2003) 574-578).*
Yazici (AJR:179, Aug. 2002).*
Fowkes, F. M., "Attractive Forces at Interfaces," The Interface Symposium—5, Industrial and Engineering Chemistry, vol. 56, No. 12, p. 40 (1964).
International Cosmetic Ingredient Dictionary and Handbook, The Cosmetic, Toiletry, and Fragrance Association, 10th Edition, vol. 4, Gottschalck, T.E. and McEwen, Jr., Eds. p. 2728 (2004).
Bio Skin Doll, Beaulax Co. Product Information, www.beaulax.co.jp/bio/index2 e.htm, 5 pages.
Tanaka et al., "The 'Haptic Finger'—a new device for monitoring skin condition," Skin Research and Technology, vol. 9, pp. 131-136 (2003).
Stockdale, M., "A Novel Proposal for the Assessment of Sunscreen Product Efficacy Against UVA," International Journal of Cosmetic Science, vol. 9, pp. 85-98 (1987).

* cited by examiner

*Primary Examiner* — David J Blanchard
*Assistant Examiner* — Garen Gotfredson
(74) *Attorney, Agent, or Firm* — John G. Powell

(57) ABSTRACT

Method of product evaluation comprising the steps of applying at least one substance to a surface of an artificial substrate to form a substance-coated surface, wherein the substrate surface demonstrates at least one physical property selected from the group consisting of a total surface energy of from about 15 mJ/m$^2$ to about 50 mJ/m$^2$, a polar component of the total surface energy of from about 0 mJ/m$^2$ to about 15 mJ/m$^2$, a zeta-potential at a pH of about 5.0 of from about −30 mV to about 30 mV, and combinations thereof, and performing at least one analysis of the substance-coated surface.

27 Claims, No Drawings

METHODS OF USE OF SUBSTRATE HAVING PROPERTIES OF KERATINOUS TISSUE

CROSS REFERENCE TO RELATED APPLICATION

This application claims the benefit of U.S. Provisional Application No. 60/772,469, filed Feb. 10, 2006; and U.S. patent application Ser. No. 11/502,858, filed Aug. 11, 2006, now U.S. Pat. No. 7,954,392 granted Jun. 7, 2011.

FIELD OF THE INVENTION

The present invention relates to methods of use of a substrate having properties of mammalian keratinous tissue.

BACKGROUND OF THE INVENTION

Many consumer products are applied to the skin or hair, and/or involve the sensory experience of touching. Consumer preferences are influenced by a multitude of factors, including product effectiveness, the feel of the product, fragrance, durability, ease of rinsing, etc. One way to determine consumer preferences is by conducting consumer marketing tests, in which a representative group of consumers, or panelists, provide feedback after using a product. Consumer marketing tests have several drawbacks, however. Because panelists must be appropriately selected and compensated for their time, such tests are expensive and time consuming. Human feedback is inherently subjective, and may raise concerns about reliability. Products must be safe for human testing, and the analyses that can be performed after application also are limited.

Some product testing can be performed using model systems. Artificial substrates are available that, to some extent, imitate human skin. For example, theatrical performers often transform their appearance by using molded body parts that can be made to look remarkably like human skin. Alternatively, keratinous tissue from animals or human cadavers may be used. Whereas these and other available models may be suitable for some types of product testing, all have significant limitations. Cadaver tissue is costly, and neither cadaver nor animal tissue truly mimics various types of living, human tissue. Artificial substrates are poorly suited to assess characteristics such as product adsorption, rinseability, elasticity and compressibility. Many substrates absorb water and/or decompose, and thus cannot be effectively cleaned or reused. Currently available models also fail to reflect differences in skin on various parts of the body, in different environments, and between different individuals, which may be critical in developing certain personal care products. Characteristics of skin on, for example, one's face, fingertips, palms of the hand, heels, and underarms tend to differ dramatically. The skin of babies and young children differs from the skin of adults, and skin having hair differs from non-haired skin.

There exists a need, therefore, to reduce testing with human subjects and to broaden the range of product testing that can be performed, by providing a method of using a substrate having properties of mammalian keratinous tissue to reproduce a range of properties most relevant to a given product.

SUMMARY OF THE INVENTION

The present invention meets the aforementioned need and describes methods of use of a substrate having properties of mammalian keratinous tissue ("substrate") developed by the applicants. A substance, examples of which are consumer products, can be topically applied to the substrate, which can be analyzed by a wide variety of methods to gain insight into properties of the substance and/or substrate. The data obtained from the analysis can provide insight into properties such as product deposition, adhesion, cleansing, feel, and appearance, which in turn can be correlated to consumer needs and preferences.

The physical properties demonstrated by the substrate include but are not limited to, surface energy (including hydrophobic and hydrophilic interactions), surface charge, surface reactivity, texture, shape and appearance. In contrast to previously available models, the texture of the substrate used in the present invention can more closely mimic a wide variety of keratinous tissues. Texture may be important in determining, for example, product deposition and coverage, in particular in areas of keratinous tissue having wrinkles and deep lines. Texture also may be important in determining whether a given product is effective, for example, in dark, moist environments produced by deep lines and folds of skin.

Optionally, one or more coating layers may be stably affixed to the surface of the substrate to more closely mimic a wider range of types of keratinous tissue and properties thereof. For example, dry skin tends to be relatively hydrophobic, whereas wet skin tends to be relatively hydrophilic. If one is interested in formulating a product that more effectively adheres to skin in the shower, a coating layer similar in hydrophilicity to wet skin can be bonded to a substrate of the present invention, the product applied, rinsed, and the surface analyzed. In addition, skin has a net charge associated with its surface, which may be dependent upon many factors, including for example perspiration, dryness, and even one's gender. A coating layer can be stably affixed to the substrate to produce a desired net positive or net negative charge, which would allow development of products better suited to these various circumstances. Substrates can be produced that combine any of the aforementioned properties, resulting in models of keratinous tissue found in a variety of environments, on a variety of body parts, and on a variety of individuals.

The methods of the present invention offer several advantages over consumer marketing tests. The substrates are cost effective, and easy to produce, store and use. The coated substrates are robust, can be effectively cleaned with a variety of solvents without substantial deterioration, and re-used. Testing can be performed more rapidly, and can more easily be repeated, resulting in increased throughput, efficiency and reproducibility. After a substance has been applied, the substrate can be analyzed using standard physical and analytical methods, which results in more objective and reliable data than can be obtained from human panelists. A wide variety of analyses can be performed, including destructive analyses, which are not possible to perform on human subjects. In addition, the physical properties can be selected that are beyond the parameters typically observed in human skin, which would, for example, allow mechanistic studies to be performed.

The following represent non-limiting embodiments of the present invention.

According to a first embodiment of the present invention, a method of product evaluation is provided, comprising the steps of applying a substance to a surface of an artificial substrate to form a substance-coated surface and performing at least one analysis of the substance-coated surface. The substrate surface demonstrates at least one physical property selected from the group consisting of a total surface energy of from about 15 mJ/m$^2$ to about 50 mJ/m$^2$, a polar component of the total surface energy of from about 0 mJ/m$^2$ to about 15 mJ/m$^2$, a zeta-potential at a pH of about 5.0 of from about −30 mV to about 30 mV, and combinations thereof. The artificial substrate further may have a texture that mimics mammalian keratinous tissue.

According to another embodiment of the present invention, a method of product evaluation is provided, comprising the steps of providing a first artificial substrate according to the first embodiment; providing a second substrate; applying a substance to at least one of the substrates to produce a substance-coated substrate; securing at least one of the substrates to an instrument capable of measuring frictional force; moving the first substrate with respect to the second substrate in a controlled manner while maintaining substantially continuous contact between the substrates; and measuring the frictional force generated by the movement of the first substrate while in contact with the substance-coated second substrate.

According to yet another embodiment of the present invention, a method of modeling the deposition of a substance onto mammalian keratinous tissue is provided, comprising the steps of applying a substance to a surface of an artificial substrate according to the first embodiment to form a substance-coated surface, and assessing the amount of substance retained on the surface of the substrate.

According to yet another embodiment of the present invention, a method of modeling the removal of a substance from mammalian keratinous tissue is provided, comprising the steps of applying a first substance to a surface of an artificial substrate according to the first embodiment to form a substance-coated surface, placing a second substance in contact with the substance-coated surface; and assessing the amount of the first substance retained on the surface of the substrate.

According to yet another embodiment of the present invention, a method of modeling adhesion of an adhesive article of manufacture onto keratinous tissue is provided, comprising the steps of placing the adhesive article of manufacture in contact with an artificial substrate according to the first embodiment to form a substrate-adhesive complex, and performing at least one analysis of the substrate-adhesive complex.

According to yet another embodiment of the present invention, a method of consumer product evaluation is provided, comprising the steps of applying a substance to a surface of an artificial substrate according to the first embodiment to form a substance-coated surface, performing at least one analysis of the substance-coated surface to produce data, and using the data to aid in product development. The substrate is comprised of material selected from the group consisting of polyurethane, polydimethylsiloxane, linear polyethylene, isotactic polypropylene, polystyrene, polyamide, and mixtures thereof, and the surface of the substrate has a texture that mimics mammalian keratinous tissue.

According to yet another embodiment of the present invention, a method is provided for using the substrate of the present invention as a calibration standard for instrumental measurements of mammalian keratinous tissue.

DETAILED DESCRIPTION OF THE INVENTION

Whereas the specification concludes with claims that particularly point out and distinctly claim the present invention, it is believed that the invention will be better understood from the following details.

The present invention provides methods of use of a substrate having properties of mammalian keratinous tissue. The methods comprise the step of applying at least one substance to a substrate, which demonstrates at least one physical property that is representative of mammalian keratinous tissue. The article of manufacture in turn may be analyzed by a wide variety of methods to gain insight into the interaction of the substance with the coated substrate.

Each of the above and additional elements is described herein.

In all embodiments of the present invention, all percentages of materials in the substrate are by weight of the total substrate, unless specifically stated otherwise. All percentages of materials in an individual coating layer are by weight of the individual coating layer, unless specifically stated otherwise. All ratios are weight ratios, unless specifically stated otherwise. The number of significant digits conveys neither limitations on the indicated amounts nor on the accuracy of the measurements. All amounts indicating quantities, percentages, proportions, etc. are understood to be modified by the word "about" unless otherwise specifically indicated.

"Topical application," as used herein, means to apply or spread a composition onto the surface of living keratinous tissue and/or onto an artificial substrate as described herein.

"Keratinous tissue," as used herein, means keratin-containing layers disposed as the outer layer of mammalian epidermal tissue, including skin, hair, nails, lips, vulvar region, buttock, and nails. The vulvar region is understood to include the region from the posterior gluteal groove and perineum to the anterior mons pubis and laterally between the intertriginous zones. The keratinous tissue may be from any part of the body of the mammal, and may vary widely in characteristics that include, but are not limited to, age, condition (for example, dryness), thickness, elasticity, pigmentation, presence of blemishes and/or imperfections, etc. "Keratinous tissue" also is understood to include the outer layer of mammalian mucosal membranes, such as the alimentary canal, including the oral cavity, esophagus, stomach, intestines, nasal cavity, lips, stomach and intestines, and the vaginal canal.

"Artificial," as used herein, means of a synthetic nature, or man-made. "Artificial substrates" may include substrates derived from naturally occurring materials, for example collagen, but which have a non-naturally occurring final form.

"Modeling," as used herein, means to simulate, or approximate, an interaction between a substance and mammalian keratinous tissue such as deposition, adhesion, cleansing, tactile perception, appearance, etc., by applying the substance of interest to a substrate as described herein which has one or more relevant properties of keratinous tissue. Data obtained from analysis of the substrate and/or substance may then be correlated to desired properties of the product, for example, as determined by consumer preferences.

"Physical property representative of mammalian keratinous tissue," or grammatical equivalents thereof, as used herein, means physical and/or chemical properties of the article of manufacture that are substantially similar to mammalian keratinous tissue and that may be relevant to a particular product or substance. For example, if the keratinous tissue is found to be hydrophobic and positively charged, the coated surface of the article of manufacture also will be hydrophobic and positively charged.

"Elongation range," as used herein, means the range that an article of manufacture may be elongated, or stretched, before breaking or alternatively, before becoming irreversibly unfit for the intended use. Herein, the elongation range is expressed as a percentage, and is calculated as the length of the article of manufacture after stretching divided by the length of the article of manufacture prior to stretching, the quotient of which is multiplied by 100.

"Texture," as used herein, means a series of impressions and/or elevated areas, relative to the average height of the planar surface of the textured layer.

"Mimics," as used herein to refer to texture, means that one of ordinary skill in the art would recognize the depth, density and arrangements of the lines and/or grooves of the article of manufacture to be similarly patterned to the keratinous tissue of interest.

"Negative mold," or "negative impression," as used herein, means a mold created by placing a suitable material on the keratinous tissue or body part of interest, and removing the material from the tissue. The resulting negative mold contains an impression of the keratinous tissue or body part. The resulting negative mold subsequently can be used to create a positive mold.

"Positive mold," as used herein, means an article made from material capable of being molded or formed so as to resemble the shape of a body part or keratinous tissue of interest. Positive molds typically are made by pouring or pressing a suitable material into a negative mold. A suitable material will retain the texture and/or shape of the keratinous tissue from which the negative mold is made.

"Substrate," as used herein, means one or more materials which may have one or more physical properties representative of keratinous tissue. "Coating layer," as used herein, means one or more chemical moieties, or coating materials, that are stably affixed to the substrate. When one or more coating layers are affixed to the substrate, the coating layer typically will determine the physical properties representative of keratinous tissue. When more than one substrate material and/or coating material is present, the materials may be homogenously mixed, may form discrete areas, and/or may form discrete layers.

"Homogenously mixed," as used herein, means that the substrate and/or coating materials are combined such that the chemical and physical properties of various areas of the substrate or coating layer are substantially uniform.

"Discrete area," as used herein, means that within a given layer, the substrate and/or coating materials are separated to form areas that predominantly comprise different materials or combinations of coating materials. This results in a substrate and/or coating layer that may have varying chemical and physical properties, depending upon which area of the layer is analyzed.

"Discrete layer," as used in reference to the coating layer, means that the coating materials form at least a first coating layer and a second coating layer. The first coating layer stably affixed to the substrate such that the thickness of the coating layer is substantially uniform, and the second layer similarly is stably affixed to the first coating layer. When used in reference to the substrate, the materials form a first layer, upon which a second layer is stably affixed. Additional layers may be sequentially added. Each layer may comprise the same or different materials. When a layer comprises more than one material, the materials may be homogenously mixed, may form discrete areas, and/or may be combinations thereof.

"Stably affixed," or alternatively "bonded," as used herein, means that a compound, for example a coating layer, is stably attached such that the compound remains substantially affixed during at least one use and analysis. "Substantially affixed" is understood to mean any amount of coating layer that may be incidentally removed is insufficient to measurably alter the physical properties of the artificial substrate surface that are representative of keratinous tissue. "Stably affixed" further means that the compound remains substantially affixed when rinsed and/or rubbed with solvents including, but not limited to, water, detergents, alcohols (for example, methanol, ethanol and isopropanol), hydrocarbons (for example, hexane). The bonding may be covalent, or may occur by any suitable means as would be understood by one of skill in the art to result in being stably affixed as defined herein. "Stably affixed" is understood not to include, for example, laminated or other coating layers which may be removed, exhibit peeling, and/or are visibly or otherwise damaged upon exposure to solvents including, but not limited to, the aforementioned solvents.

"Stable," as used herein, means that the chemical and/or physical properties of the article of manufacture do not change significantly under reasonable conditions of use, including cleaning, transport and storage conditions. When used in reference to one or more coating layers, "stable" means that significant amounts of the coating layer are not removed during use, non-destructive types of analysis, and/or cleaning.

"Re-used," as used herein, means that a substance may be applied to the article of manufacture and data reliably obtained at least twice.

"Analysis," as used herein, means analysis of chemical and/or physical properties of the substrate and/or the substance that has been applied to the substrate. Analysis may be quantitative and/or qualitative, and occur through a variety of means that would be known to one of skill in the art, including but not limited to instrumental, chemical, and sensory analyses.

"Substance deposition," as used herein means the transfer of at least a portion of a substance, or of one or more components of a substance, from an applicator to a substrate or to keratinous tissue.

"Substance adhesion," as used herein means the ability of an article of manufacture and/or a substance to remain attached to a substrate or to keratinous tissue for a desired period of time and/or under desired conditions.

"Adhesive article of manufacture," as used herein means an article of manufacture such as tape, a bandage, patch, etc., designed to remain attached to a substrate or to keratinous tissue for a desired period of time and/or under desired conditions and which can then be removed without causing significant damage to the substrate. The adhesive article of manufacture may comprise a discrete adhesive, or may adhere through physical properties of the article itself.

1. Article of Manufacture

A. Substrate

The artificial substrate of the present invention demonstrates at least one physical property that is representative of mammalian keratinous tissue. One or more coating layers may be stably affixed to a surface of the substrate. The substrate may be smooth or textured, rigid or pliable, and may be elastic or inelastic. The substrate material may be curable, moldable, etchable, or otherwise capable of being imparted with a desired textured surface, and may comprise polymers, glass, moldable fiberglass, metals, fabrics, natural materials, and combinations thereof. In one embodiment, the substrate has an elongation range of less than 400%, alternatively less than 200%, and alternatively less than 100%. The substrate may be formed by, for example, using a negative mold, into which a suitable material is poured and/or pressed; extruding; and/or imprinting, etching, engraving, or otherwise imparting a texture, including with the use of a laser and/or chemicals, to a solid surface. The substrate further may comprise at least two materials, which may be homogenously mixed, may form discrete areas and/or may form discrete layers.

Examples of suitable materials are disclosed in U.S. Pat. No. 6,558,422, issued to Baker et al., and include, but are not limited to polypropylene, isotactic polypropylene, polyethylene, branched polyethylene, linear polyethylene, polyethylene oxide, polyethylacrylate, polyethyleneterephthalate, polyurethane, aliphatic polyurethane, polyester, polyorthoesters, polylactic acid, polyglycolic acid, polyethylene glycol, collagen, polygalactic acid, polydioxanone, polytrimethylene carbonate copolymers, poly-ε-caprolactone homopolymers and copolymers, polyanhydrides, poly-α-methylstyrene, polyamide 12, polyamide 6,6, polybutylmethacrylate, polycarbonate, fluoropolymers (including polychlorotrifluoroethylene, polytrifluoroethylene, polytetrafluoroethylene, polyvinylfluoride, polyvinylidenefluoride), polyvinylchloride, polyvinylidene chloride, polydimethylsiloxane, polyetheretherketone, polymethylmethacrylate, polyethylmethacrylate, polyhexylmethacrylate, polyisobutylene, polyisobutylmethacrylate, polymethacrylic acid, polymethylacrylate, polystyrene, poly(t-butylmethacrylate), polytetrahydrofurane, polytetramethylene oxide, polyvinylacetate, polyvinyltoluene, copolymers, isomers and derivatives of any of the foregoing, and mixtures thereof. The substrate further may be comprised of metals and metal alloys, including steel, nickel, gold, silver, and mixtures thereof. In one embodiment, the substrate material is selected from the group consisting of polyurethane, polydimethylsiloxane, linear polyethylene, isostatic polypropylene, polystyrene, polyamide, and mixtures thereof. Alternatively, the substrate material is polyurethane.

Other examples of substrates that may be suitable include, but are not limited to, Vitro-Skin™ and Vitro-Corneum®, both available from IMS Inc., Milford, Conn.; Bioskin, available from Beaulax; Test Skin™ 11, available from Organogenesis, Inc., Canton, Mass., Skinethic®, from Skinethic Tissue Culture Laboratories, Nice, France, EpiDerm™ available from MatTek Corp., Ashland, Mass. collagen substrates, for example COFFI films, and combinations thereof.

The substrate may be in any shape or form suitable for application of a substance and for analysis of the substrate and/or coating layer. In one embodiment, the substrate is in the form of a sheet having two substantially planar, parallel surfaces, and a substantially uniform thickness. In one embodiment, the thickness of the substrate is from about 0.001 mm to about 5.0 cm. Alternatively, the thickness of the substrate is from about 0.01 mm to about 1.0 cm. Alternatively the thickness of the substrate is from about 0.1 mm to about 0.5 cm. In another embodiment, the substrate is substantially cylindrical, and has an average diameter of from about 0.001 mm to about 3.0 cm, alternatively from about 0.01 mm to about 1 cm, alternatively from about 0.1 mm to about 1.0 mm, and alternatively from about 0.01 mm to about 0.2 mm. In one embodiment, the form of the substrate resembles mammalian fur. Alternatively, the form of the substrate resembles human hair. Alternatively, the form of the substrate resembles a sample of human hair, such as a swatch or ponytail. In another embodiment, the substrate is in the form of a body part, for example, a head, face, arm, leg, hand, foot, finger, toe, upper torso, lower torso, buttocks, external genitalia and/or pelvic region. Alternatively, the substrate is in the form of a child's buttocks and/or pelvic region.

The substrate may be colored, white or colorless, and may be transparent or opaque. In one embodiment, the substrate is similar in color to a desired type of mammalian skin. Alternatively, the substrate is similar in color to human skin. Alternatively, the color may be altered to resemble various degrees and types of pigmentation found in human skin.

B. Texture

The substrate may comprise at least one textured surface to mimic a desired type of mammalian keratinous tissue. When the substrate is cylindrical, the outermost surface may be textured. The substrate may be textured, and/or the texture may result from the coating layer if present. The texture comprises a plurality of impressions and/or elevated areas that may be patterned and/or may be randomly arranged. The topography of the texture may vary to resemble degrees of wrinkling of keratinous tissue. Alternatively, the depth of the impressions may vary to resemble keratinous tissue ranging from relatively smooth (for example, oral mucosal linings) to deeply lined (for example, elbows or deep facial lines), and further may resemble scaly, fissured, rough, and/or otherwise visibly-textured keratinous tissue. The texture may resemble the topography of keratinous tissue on essentially any body part. The texture may resemble the topography of healthy keratinous tissue or alternatively keratinous tissue damaged by, for example, exposure to UV-rays, chemicals, and/or illness. Alternatively, a substrate may comprise discrete areas having different textures. The texture may be visible without the use of visual aids, (i.e., on a macroscopic level), or may be clearly visible only with visual aids such as a magnifying glass or microscope set at a 10× or 100× magnification setting. In one embodiment, the texture mimics the topography of mammalian keratinous tissue. Alternatively, the texture mimics the topography of human keratinous tissue. Alternatively, the texture mimics the topography of human skin. Alternatively, the texture mimics the topography of the outermost layer of mammalian hair. Alternatively, the texture mimics the topography of the outermost layer of human hair. Alternatively, natural or artificial hair may be attached or anchored in the substrate such that one end protrudes outwardly through the coating layer. Alternatively, the texture mimics a composite of topographies of keratinous tissue from a plurality of individuals, representative of an average keratinous tissue type of a given population.

The impressions may be in the form of, for example, lines or grooves, the depth of which may vary depending upon the type and condition of keratinous tissue upon which the substrate is modeled. In one embodiment, the impressions have a depth of from about 0.001 mm to about 10 mm, alternatively from about 0.001 mm to about 0.1 mm, alternatively from about 0.1 mm to about 1 mm, and alternatively from about 0.1 mm to about 0.5 mm, as measured from the average height of the planar surface of the substrate.

C. Coating Layer

The substrate of the present invention may comprise at least one coating material that is stably affixed to the first surface of the first layer. The thickness of the coating material may be substantially uniform. In one embodiment, the coating material is covalently bonded to a textured surface of the first layer, and alternatively is affixed by means of plasma deposition. The coating material may impart to the first layer at least one physical property that is representative of mammalian skin, and the choice of coating material(s) will depend upon the desired physical property. When more than one coating material is used, the compounds may be homogenously mixed and/or may form discrete areas. In one embodiment, a first discrete coating material is stably affixed to the first surface of the first layer, and at least one additional coating material is stably affixed to the first coating material. The additional coating materials may be made from the same or from different coating materials than the first coating material. The thickness of the coating material may vary, but when the underlying first layer is textured, the coating material may be sufficiently thin so as not to mask or significantly interfere with an underlying texture, and may faithfully mimic the underlying substrate topography. In one embodiment, the thickness of an individual coating material is a monolayer. Alternatively, the thickness of an individual coating material is from about 0.1 nm to about 1 mm, and alternatively from about 1 nm to 0.1 mm.

Examples of classes of suitable coating materials, as well as properties representative of mammalian skin, are described in U.S. patent application Ser. No. 11/502,858. Suitable coating materials include, but are not limited to, chemical functional groups, organic compounds, hydrocarbons, chemically functionalized hydrocarbons, macrocycles, lipids, proteins, amino acids, hydrophilic monomers, hydrophobic monomers, polymerizable monomers, metals, particulates, and combinations thereof. Additionally or alternatively, the coating material may comprise particulate materials and/or fibrous materials. In one embodiment, the coating materials are hydrocarbons, for example, pentenes, hexenes and combinations thereof; chemically functionalized hydrocarbons, for example allyl amines, allyl alcohols, carboxylic acids, sulfides, thiosulfides, and mixtures thereof; chemically functionalized hydrocarbons modified with at least two distinct functional groups; hydrophilic monomers; hydrophobic monomers, for example, perfluoromethylcyclohexane (PFMCH) monomer; polymerizable monomers, and combinations thereof. In one embodiment, the coating material is selected from the group consisting of allyl amine, allyl alcohol, 1,1,1-trimethyl-1-pentene, perfluoromethylcyclohexane, and mixtures thereof.

D. Bonding of Coating Layer

The coating layer may be stably affixed to the substrate and/or other coating layer by any process which results in formation of a stable coating layer. The process may result in covalent bonds being formed between the coating layer and the substrate, or alternatively between two coating layers, or the process may result in other types of stable bonds. The bonding process may require the steps of surface activation; deposition of the coating material; and bonding the coating material to the activated substrate. Alternatively, curing may be required to further stabilize the coating material.

Surface activation may be required to make the surface chemically reactive and thus prepare the substrate for deposition of a coating layer. Surface activation may occur by a variety of means, non-limiting examples of which include plasma activation, electron beam activation, corona activation, glow discharge activation, optical activation, and combinations thereof. Surface activation may occur either at or below atmospheric pressure. In one embodiment, surface activation occurs by means of plasma activation. Plasma activation may occur with radio-frequency generated plasma or with microwave-frequency generated plasma. An example of a suitable atmospheric-pressure plasma generating apparatus and bonding process is described in U.S. Pat. No. 6,821,379, issued to Datta et al. An example of a suitable microwave-frequency generated plasma apparatus and bonding process is described in U.S. Pat. No. 6,841,201, issued to Shanov et al.

Deposition of the coating material also may occur through a variety of means, non-limiting examples of which include exposure of the activated surface to the coating material in the gas phase and/or exposure to the coating material in the liquid phase, for example by spin coating, spray coating, or dip coating, provided that the deposition results in a stably bonded coating layer. Processes that result, for example, in a laminated coating that can be manually peeled or removed by rubbing and/or with commonly available solvents are not considered to be stably affixed, as defined herein. In one embodiment, the coating material is deposited in the gas phase, for example by plasma deposition. Alternatively, the coating material is deposited by means of flash evaporation and cryo-condenstation.

Bonding and/or curing may be required subsequent to deposition to sufficiently adhere the coating layer to the substrate and to otherwise stabilize the coating layer. Methods of bonding include, but are not limited to, polymerization, cross-linking, including e-beam crosslinking, photo-crosslinking, and/or thermal cross-linking, and combinations thereof. The methods of inducing chemical bonding may include application of energy in the form of heat, light, radio-frequency, microwave, and/or ultrasound energy. The energy may be applied in a pulsed and/or continuous manner.

Alternatively, activation, deposition and/or bonding may occur by means of a single process. For example, both surface activation and deposition (or "grafting") may occur as a result of the plasma deposition process described in U.S. Pat. No. 6,821,379, issued to Datta et al., and U.S. Pat. No. 6,841,201, issued to Shanov et al.

E. Physical Properties Representative of Mammalian Keratinous Tissue

The substrate demonstrates one or more physical properties that are representative of mammalian keratinous tissue. The property or properties of interest will vary according to factors that include, but are not limited to, the type of keratinous tissue, the environment of the keratinous tissue, the individual consumer, the substance that is being applied to the keratinous tissue and/or the product with which the keratinous tissue comes into contact. Examples of representative properties include, but are not limited to, surface energy (for example, hydrophobicity and hydrophilicity), surface charge, surface reactivity, texture, appearance, form, and combinations thereof. The properties can be controllably varied by, for example, the choice of substrate and/or coating layer, and by varying parameters that control deposition of the coating layer.

The coating layer may have an average surface charge that is representative of mammalian keratinous tissue. Herein, the surface charge of the coating layer is understood to mean the average surface charge of a representative area of coating layer, although localized variations may occur due to such factors as variation of deposition of coating materials (e.g., proteins and lipids) and texture. The surface charge of the coating layer may be positive, negative, or neutral, and is largely determined by the presence of ionic species, including acidic and basic species. The surface charge determines, for example, the polarity of the keratinous tissue, which in turn may affect deposition and adhesion of various substances on the surface. The net surface charge may be measured by determination of the isoelectric point and/or the zeta-potential of the surface. A variety of means of determining the zeta-potential may be employed and would be known to one of skill in the art. For the purposes of the present invention, determine the zeta-potential of the coated substrates by streaming potential measurements conducted on an Electro Kinetic analyzer (model no. BI-EKA, Anton Parr GmbH, Brookhaven Instruments Corporation, New York, N.Y.) with a clamp cell configuration, using as an electrolyte solution $1.0 \times 10^{-3}$ M KCl in deionized water, titrated starting from a pH of about 2.5 to a pH of about 8.0 using a 1N solution of NaOH. The zeta potential values generated as a function of pH are relative to standard PMMA (polymethyl methacrylate). Each zeta-potential profile (for each type of coated substrate and other model) can thus be compared in relative terms.

In one embodiment, the zeta-potential of the coating layer at a pH of about 5.0 is from about −30 mV to about +30 mV, where "mV" means $1 \times 10^{-3}$ Volts. In one embodiment, the zeta-potential of the coating layer at a pH of about 5.0 is from about −15 mV to about +15 mV.

The coating layer may have an average surface energy that is representative of mammalian keratinous tissue. Herein, the surface energy of the coating layer is understood to mean the average surface energy of a representative area of coating layer, although localized variations may occur due to such factors as variation of deposition of coating materials (e.g., proteins and lipids) and texture. The surface energy of the coating layer correlates to hydrophobicity and hydrophilicity, and may be representative of, for example, the moisture content of skin. The surface energy of the coating layer are derived from contact angle measurements, which can be converted to surface energy by various accepted models that would be known to one of skill in the art. One such model, used in the present invention, is the Fowkes equation, as described in Fowkes, F. M.: *Industrial and Engineering Chemistry*, vol. 56, number 12, p. 40 (1964):

$$\gamma_{lv}(1+\cos\theta)=2(\gamma_{lv}{}^d\gamma_{sv}{}^d)^{1/2}+2(\gamma_{lv}{}^p\gamma_{sv}{}^p)^{1/2}$$

where $\theta$ refers to the contact angle; $\gamma_{lv}$ refers to the surface tension of the liquid; $\gamma_{lv}{}^d$ refers to the dispersive component of the surface tension of the liquid; $\gamma_{sv}{}^d$ refers to the dispersive component of the surface tension of the solid; $\gamma_{lv}{}^p$ refers to the polar component of the surface tension of the liquid and $\gamma_{sv}{}^p$ refers to the polar component of the surface tension of the solid. The contact angles of the coated substrates of the present invention were measured using diiodomethane (99%, Aldrich), ethylene glycol (99%+, Aldrich) and water (HPLC grade, Aldrich).

The total surface energy of the coating layer is the sum of the dispersive surface energy component and the polar surface energy component, which is thought to affect properties such as adhesion of substances to the coating layer. In one embodiment, the coating layer has a total surface energy of from about 15 mJ/m$^2$ to about 50 mJ/m$^2$, alternatively from about 20 mJ/m$^2$ to about 40 mJ/m$^2$ and alternatively from about 28 mJ/m$^2$ to about 35 mJ/m$^2$, where "mJ" means $1\times10^{-3}$ Joules and "m$^2$" means square meters. In one embodiment, the coating layer has a polar surface energy component of from about 0 mJ/m$^2$ to about 15 mJ/m$^2$. Alternatively, the polar surface energy component is from about 0 mJ/m$^2$ to about 5 mJ/m$^2$, alternatively from about 7 mJ/m$^2$ to about 13 mJ/m$^2$, and alternatively from about 13 mJ/m$^2$ to about 20 mJ/m$^2$.

The coating layer may have a surface reactivity that is representative of mammalian keratinous tissue. Surface reactivity is understood to include an increased tendency to react with, or alternatively to bond to, a given compound. Surface reactivity may be determined by a variety of methods, including, for example, measurement of binding coefficients. In contrast to surface charge, which relates to the presence of ionic species, surface reactivity is understood to encompass other types of chemical interactions, for example, covalent interactions. One non-limiting example of surface reactivity would be that exhibited by a thiol-containing coating material toward nucleophilic chemical moieties, for example gold or silver, in products and/or substances.

II. Method of Use

The present invention describes methods of use of the substrate described herein, comprising the step of applying one or more substances to the surface of the substrate to form a substance-coated surface. The substrate surface has properties similar to keratinous tissue, including but not limited to surface energy, surface charge, texture, shape and/or appearance. The methods of use may include a method of product evaluation, wherein a substance is applied to the substrate or wherein the substrate is used in instrumentation capable of measuring frictional force. The methods of use may further include modeling the deposition and/or adhesion of a substance onto mammalian keratinous tissue; and the cleansing, or removal, of a substance from keratinous tissue.

The substance may be applied directly to the substrate, for example with one's hand or with an implement, or may be applied by transfer from an article of manufacture or second substrate. Alternatively, the substance may be applied and an article of manufacture subsequently brought into contact with the substrate, for example, to measure the absorbancy of the article of manufacture. Non-limiting examples of suitable articles of manufacture include absorbent products, such as facial tissue, facial cleansing pads, toilet tissue, paper towels, catamenial pads, and tampons; baby care products, including diapers, wipes, cleansers, conditioners; adult incontinence products; and combinations thereof.

The method further may comprise the step of performing one or more analyses of the substrate, the article of manufacture, and/or the substance of interest. The substance may be removed from the substrate, for example by rinsing, wiping, or other suitable means, prior to, during and/or after analysis. In one embodiment, the steps of applying a substance, performing analysis, and optionally removing the substance, may be repeated at least once, alternatively at least five times, alternatively at least ten times, and alternatively at least twenty times.

The substance may be a product, for example a consumer product, a natural substance, and/or an imitation of a natural substance. The consumer product may be marketed, intended to be marketed, or have the potential to be marketed to consumers. Examples of products include, but are not limited to, skin care products, including moisturizers, cleansers and combinations thereof; perfumes and perfume raw materials, whether alone or as part of a composition; cosmetics; pharmaceutical products and/or compositions comprising pharmaceutical ingredients; neutraceuticals, for example vitamins, minerals, herbal products and other plant extracts and/or compositions comprising neutraceuticals; hair care products, including shampoos, conditioners, styling agents, bleaches, colorants, and combinations thereof; deodorants; antiperspirants; perfumes; deodorizers; fabric care products, including softeners, detergents, cleansers, whiteners and deodorizers; household cleansing products, such as dish detergents, surface cleaners, disinfectants, soaps, etc.; and combinations of any of the foregoing. Examples of natural substances include, but are not limited to, water, bodily fluids such as blood, menstrual fluid, urine and breast milk; bodily waste, such as feces and mucosal secretions; plant products, for example, grass stains, pollen and other allergens; and combinations of these and/or any of the aforementioned products. Alternatively, the substance may be an imitation of any of the aforementioned natural substances, which has properties similar to those of interest in the natural product. Alternatively, the substance may be one that may stain under given circumstances, non-limiting examples of which include ink, wax crayons, dyes and colorants, etc.

A wide variety of amounts of substance may be applied to the article of manufacture, and will depend upon such factors as the substance and the intended use thereof. In one embodiment, the amount of substance applied is the amount of a particular substance that a consumer is instructed to topically apply, or alternatively, the amount of a substance that a consumer would reasonably be expected to topically apply. Alternatively, the amount of substance applied represents an amount that would be expected to occur as a result of bodily functions, or of physical activities, for example, sweat resulting from physical activity or stains in clothing resulting from playing outdoors. In one embodiment, the amount applied to the article of manufacture is from about 0.1 mg/cm$^2$ to about 1.0 g/cm², alternatively from about 0.5 mg/cm² to about 0.5 g/cm² and alternatively from about 1 mg/cm² to about 0.1 g/cm².

The methods of the present invention may be performed under static conditions or with dynamic movement, at room temperature, or at body temperature. Alternatively, the substrate may be pre-conditioned to specified environmental conditions, for example, temperature, humidity, UV-radiation, light, exposure to additional substances, etc. Alternatively, the substance may be applied with the aid of an energy delivery device, such as an ultrasonic, ultraviolet, or heat energy delivery system. Alternatively, the substances may be applied with a delivery enhancement device, non-limiting examples of which include an implement, such as a sponge or sponge-tipped applicator, a spray applicator, a brush, and combinations thereof.

In one embodiment, a method is provided for the use of a substrate described herein in an instrument capable of measuring frictional force, non-limiting examples of which include tensiometers, such as a Texture Analyzer Plus™, a tribometer, and/or Instron™ instruments. The frictional force in turn may be correlated to the tactile perception, or "feel," of a product, for example, running one's fingers through washed and/or conditioned hair, stroking a washed dish, feeling one's skin after applying a moisturizer; the feel of the mouth, gums, lips, etc. after use of an oral hygiene product, tackiness, softness, glide, slipperiness, oiliness or greasiness, "squeaky clean" feel, etc. A variety of suitable instruments is commercially available or may be assembled, and would be known to one of skill in the art. A suitable substrate (first substrate) may be secured to the instrument, and used as a sensing element. The substrate may be textured or untextured, and may comprise a coating layer or be uncoated. In one embodiment, a substance may be applied to the substrate to produce a substance-coated first substrate. A substance may be applied to a second substrate, non-limiting examples of which include a substrate as described herein, a sample of artificial skin, a sample of artificial hair, mammalian fur and/or human hair; household goods such as dishes, fabrics; substances representative of household surfaces, etc., to produce a substance-coated second substrate. The first substrate and substance-coated second substrate may be placed in direct contact and moved in a controlled fashion relative to each other. In one embodiment, the movement is repeated. In one embodiment, the movement simulates conditions of actual use. The coefficient of friction is measured as the substrate and substance-coated second substrate are moved. Optionally, a solvent, for example water or a cleansing solution, may be allowed to flow or otherwise contact the substrate prior to and/or during analysis.

In one embodiment, a method is provided for modeling the deposition of a substance onto keratinous tissue. A substance may be applied to the substrate, and the retention of the substance or a component thereof on the substrate may be assessed. Retention also is understood to include the uniformity of deposition, for example, the uniformity of the thickness of an applied substance, or of the concentration of a given substance per unit of area. Retention also may be assessed by monitoring the release of a substance after deposition, for example, the release over time of a perfume raw material. Alternatively, the substance not deposited onto the substrate (for example, the substance retained on an applicator) may be analyzed. In one embodiment, the applied substance is at least partially removed from the substrate prior to analysis of the substance and/or substrate. Removal may occur, for example, by rinsing with water or other solvents, wiping, and/or blotting with a second article of manufacture, evaporation, etc. Alternatively, the remaining substance may be eluted or otherwise removed from the substrate using appropriate chemical means, and optionally the amount of substance in the eluent determined. Alternatively, a method is provided for determining the effectiveness of electrospray deposition of substances. For example, a substance may be applied to a substrate as described herein by means of electrospray deposition, and suitable analyses performed as described herein.

In one embodiment, a method is provided for modeling the removal, or cleansing, of a substance from mammalian keratinous tissue. One non-limiting example of a method for evaluating the cleansing capability of a product includes the steps of applying a first substance to a substrate having properties of keratinous tissue of interest to form a substance-coated substrate; applying a second substance, for example, a cleansing composition, to the substrate by rinsing, wiping, dipping, rubbing, or other suitable means; and analyzing the substrate to assess or to quantify the amount and/or type of substances remaining on the substrate. Alternatively, the second substance may be applied to a wipe, for example, a non-woven wipe, to form a wipe product. Alternatively, the second substance may be applied by means of a delivery enhancement device. Alternatively, the method may comprise the step of applying energy to the substance-coated substrate. In one embodiment, the first substance is a cosmetic and/or skin care composition. Alternatively, the first substance is a natural or imitation substance such as sebum, dirt or other impurity. Alternatively, the first substance is a chromophore, an ink, or a similar substance that may produce a permanent or semi-permanent marking. In one embodiment, the second substance is water, a solvent, a personal care composition such as a skin cleansing composition, facial cleansing composition, exfoliating composition, mask, etc., and combinations thereof.

In one embodiment, a method is provided for adhesion of a substance and/or an adhesive article of manufacture onto the substrate. Examples of adhesive articles of manufacture include, but not limited to, bandages, temperature change devices, heat delivery systems, transdermal delivery devices, patches for delivery of skin care actives, masks (for example, facial masks comprising a skin care active), and combinations thereof. The device may adhere to the keratinous tissue and/or substrate by means of an adhesive layer, or may have no discrete adhesive layer. One non-limiting example of a method for evaluating adhesion includes the steps of applying an adhesive article of manufacture to a substrate having properties of keratinous tissue of interest (for example, surface energy, surface charge, texture, and/or shape of a body part) to form a substrate-adhesive complex; optionally exposing the substrate-adhesive complex to, for example rinsing, cleansing, or environmental conditions; optionally subjecting the substrate with the adhered article of manufacture to movement, such as bending and/or twisting; and performing at least one analysis of the substrate-adhesive complex. Alternatively, the adhered article of manufacture may be removed by mechanical means, and the force required for removal measured. Alternatively, the underlying substrate may be analyzed after removal, for example, to assess the presence of adhesive residue, transfer of actives, changes in the substrate, etc.

Alternatively, a method of consumer product evaluation is provided, comprising the steps of applying a substance to a surface of an artificial substrate to form a substance-coated surface, performing at least one analysis of the substance-coated surface to produce data, and using the data to aid in product development. Alternatively, the same substance may be applied to human keratinous tissue, data collected, and a comparison made between the interaction of the substance with the artificial substrate and with human tissue.

Alternatively, the substrate may be used as a calibration standard for instrumental measurements. The substrate, or alternatively a series of substantially similar substrates may be made having a desired property, for example texture, form or appearance, as described herein. The substrate(s) may include a series of markings having a measured dimension. The measured dimensions may vary incrementally. Examples of suitable markings include, but are not limited to, lines having a measured depth and/or length to represent wrinkles; indentations having a measured diameter and/or depth, representing pores; discrete areas of color having measured size, absorbance and/or refraction, to represent pigmentation and overall skin tone. The standards may be analyzed by a suitable instrument to produce a calibration curve, which may be used to quantify the same characteristic on, for example, mammalian keratinous tissue.

Other properties of products that may be modeled by applying a substance to a substrate as described herein include, but are not limited to, glide; greasiness; stickiness; smoothness; stability of a product and/or substance; changes in physical properties such as color, opacity, odor and texture; and combinations of any of the foregoing.

EXAMPLES

Example 1

The following example illustrates a process of creating a mold and imparting to the substrate a texture that has been modeled directly from the skin.

A first negative imprint of keratinous tissue may be made by applying a material[1] capable of forming a cast, or mold, onto a body part, for example, human skin and/or hair. The cast is removed and allowed to dry for 3-7 min. A positive mold that resembles the body part in both form and texture is then created by placing for example silicone or other suitable material[2] in the negative mold. The positive mold is impressed into polyurethane or other suitable material to create a second negative mold, and the second negative mold is allowed to cure overnight. Optionally, the positive molds are pressed into a unitary mold of polyurethane or other suitable material to create multiple negative molds. Optionally, the second negative mold is coated with a 1:1 mixture of Skin-Flex SC-89[3] stretch paint (aliphatic polyurethane gloss paint) and Skin-Flex SC-89 thinner[4] to create a first substrate having a thickness of from about 100 µm to about 600 µm, and allowed to dry for at least 12 hours. A substrate material[5] is then poured into the second negative mold (onto the gloss paint, if present) in an amount sufficient to produce a substrate having a thickness of approximately 0.1 mm-1 cm.

[1] Suitable materials include PLY-O-LIFE™ and ALGIFORM™ casting material, both available from Pink House Studios (St. Albans, Vt.); or other suitable equivalent materials.
[2] Other suitable materials include dental materials, liquid rubber, room temperature vulcanized (RTV) rubber, plastic, or equivalents thereof.
[3] SC-89 Stretch Paint, available from Burman Industries (Van Nuys, Calif.).
[4] SC-89 Thinner, available from Burman Industries, (Van Nuys, Calif.).
[5] TC-410 polyurethane, Part A (aromatic diisocyanate based pre-polymer, plasticizer mixture) and Part B, polyurethane curing agent, for example, polyether polyol, di (2-ethylhexyl) adipate, aromatic amines, aryl mercuric carboxylate) with Parts A and B in a 1:1 ratio. Optionally, Part C (Plasticizer-ester) may be included at a level of 1% to 150% by weight of the combination of Parts A and B. An acceptable alternative to TC-410 parts A and B is Skin Flex, Part A (aromatic diisocyanate terminated polyoxypropylene glycol mixture); Part B, polyurethane curing agent (polyol-diamine mixture), with Part A and Part B in a 1:2 ratio; and optionally Skin Flex Part C (Plasticizer-ester) at a level of 1% to 150% by weight of the combination of Parts A and B; all available from BJB Industries (Tustin, Calif.).

Example 2

The following illustrates one example of the process for making a suitable substrate:

Combine equal amounts of Part A and Part B of TC-410 polyurethane, or equivalent materials, and thoroughly mix. Slowly pour a sufficient amount of the mixture into a desired mold, starting from the edge and gradually moving to the center of the mold. The amount should be sufficient to produce a substrate having a thickness of approximately 0.1 mm-1 cm. One example of a suitable amount is 25 ml in a mold having an area of 7 cm×14 cm. Allow to cure overnight. Begin peeling the polymer substrate from the mold, starting from the edge. Cut away the border if necessary. When poured into a mold as described in Example 1, the substrate thus made has the texture of human keratinous tissue of the body part used to make the first negative imprint.

Example 3

The following example illustrates a process of directly imparting a texture to a substrate surface.

A patterned surface resembling the surface of mammalian keratinous tissue, for example forearm skin, or hair, is mechanically etched onto a metallic surface, following standard procedures of photolithography known to one of skill in the art. First, a pattern is created that resembles the texture of human skin, for example, from the forearm. This can be done as a computer-simulated image, or as an actual image (e.g., photographic, microscopic) from the human body part of interest. The pattern is transferred to a clear sheet to form a mask. The mask is placed onto a copper, brass or other appropriate metallic sheet, upon which a photoresist has been previously adhered or laminated. A variety of photoresists are available commercially, for example DuPont™ MX series dry film photoresists. The selection of the photoresist is based on the desired size, texture and/or feature of the keratinous tissue-texture. The composite of metal/photoresist/mask is exposed to an appropriate dose of UV light, using industry standard exposure tools. The mask is removed, the photoresist is developed and the metal layer is etched using appropriate etching solutions, as described in standard textbooks on second level microelectronics packaging.[1]

A 1:1 mixture of Skin-Flex SC-89 Stretch-paint and Skin-Flex SC-89 Thinner, as described in the previous examples, is poured into the metallic mold and allowed to dry overnight. The amount of mixture poured is adjusted, according to the size of the mold, to yield a final substrate that is typically between 600 to 800 micrometers thick. After overnight drying, the substrate material is carefully peeled off of the metallic mold as described above. The substrate material may be surface-modified, or fixedly coated, to impart more specific skin surface properties.

[1] Donald Seraphim, Ronald Lasky and Che-Yu Li: "Principles of Electronic Packaging," Mc-Graw Hill Inc. (1989).

Example 4

The following example illustrates a process for stably affixing a suitable coating material to a substrate by means of plasma coating.

Plasma deposition is performed in a plasma unit consisting of a cylindrical vacuum chamber having a diameter of approximately 30.5 cm and a length of 61.0 cm. Vacuum is produced by means of a Leybold PCS 25 vacuum pump. The RF energy is supplied from a PE 1000 Advanced Energy 40 kHz power supply, across a set of parallel Al-electrodes in the vacuum chamber. Plasma is created in the vacuum chamber, between the two electrodes, upon application of the RF power, and the effective plasma treatment area is approximately 40 cm by 20 cm.

Plasma deposition is achieved through the following process: The substrate material (sample) is placed on a perforated aluminum sample tray in between parallel plate aluminum electrodes in the plasma chamber. The chamber base pressure is reduced to approximately 100 milliTorr (mTorr). A mixture of argon and nitrogen gas, at flow rates of 20 sccm of Ar and 10 sccm of nitrogen, (where "sccm" means standard cubic centimeter per minute) is allowed to flow into the chamber for about one hour to help degas the sample to be coated. The base pressure is then reduced to 10 mTorr, and 25 W continuous wave RF power is applied for approximately 5 minutes while allowing the argon/nitrogen mixture to flow into the chamber at the same flow rates. The Ar and N2 flow is then stopped, the chamber evacuated again to 10 mTorr, and the coating material[1] (monomer) is introduced to the chamber to a pressure of 100 mTorr, with a flow rate selected in the range of 10 sccm to 200 sccm, depending on the monomer used. Continuous wave radiofrequency (RF) power at 25 W is applied for 25 minutes while maintaining a vapor pressure of approximately 100-120 mTorr. This leads to the deposition of the monomer onto the sample surface in the form of a polymeric coating that is covalently bonded to the sample surface. Instead of 25 W continuous power, RF power can be applied in the pulsed mode, with on/off time ratios of 1 to 1000, and on times in the range of 10 microseconds to 1 sec, to fine-tune the chemical nature of the coating on the sample surface. Power source can also be varied between microwave (MW) and RF, with frequencies selected from available and allowed ranges for MW or RF sources. The power is turned off, and the flow of the coating material stopped. The chamber is purged with 20 sccm Ar for approximately 30 min. The plasma coated surfaces are removed from the chamber and the contact angle, surface charge and the thickness of the coating layer determined by video contact angle measurement system (VCA-2500 from ASM), zeta-potential measurement (Anton Parr Electrokinetic Analyzer, Model BI-EKA) and Atomic Force Microscopy (Q-Scope 250 from Quesant Corporation) methods. The plasma coating process can be performed with more than one monomer, used either together to form a combination coating with polymeric species generated from both monomers simultaneously, or as separate coating layers resulting from each monomer applied separately and sequentially.

[1] Suitable coating materials include allylamine (98%, $C_3H_7N$, available from Aldrich, CAS 107-11-9); 1,1,1-trimethyl-1-pentene; 2,4,4-trimethyl-1-pentene (both available from Aldrich); allyl alchol ($C_3H_6O$, CAS 107-18-6, from Aldrich); and perfluoromethylcyclohexane monomer ($C_6F_{11}$, $CF_3$, CAS 355-02-2 (available from Avocado Chemicals). However, one of skill in the art will understand that a variety of coating materials, as described herein, may be used, the choice of which will be determined by the surface property of the keratinous tissue that one desires to reproduce.

The following chart summarizes measurements performed as described herein on various substrates.

| Substrate | Dispersive Component of Total Surface Energy (mJ/m²) | Polar Component of Total Surface Energy (mJ/m²) | Total Surface Energy (mJ/m²) | Zeta-Potential (mV)[1] | Contact Angle in degrees (H2O) | Contact Angle in degrees (Diiodo-methane) | Contact Angle in degrees (ethylene glycol) | Stable[17] |
|---|---|---|---|---|---|---|---|---|
| Normal Skin[2] | 30.30 | 0.20 | 30.50 | | | | | N/A |
| Winter Skin[3] | 29.50 | 0.06 | 29.60 | | | | | N/A |
| Summer Skin[4] | 29.70 | 3.10 | 32.80 | | | | | |
| Wet Skin[5] | 25.85 | 11.31 | 37.16 | | | | | N/A |
| Scalp[6] | 29.30 | 12.70 | 42.00 | | | | | N/A |
| Lips[7] | 33.00 | 5.50 | 38.50 | | | | | N/A |
| Bicomponent polyurethane (TC-410)[8] | 47.31 | 2 | 49.31 | (−) 22 | | | | Yes[22] |
| Polyurethane substrate with allyl amine coating layer[9] | 32 ± 1.5 | 12 ± 1.5 | 45 ± 1.0 | (+) 8.4 | 65 ± 2 | 41 ± 2 | 33 ± 1.0 | Yes[20] |
| Polyurethane substrate with plasma deposited allyl alcohol coating layer[10] | 28.9 | 12.6 | 41.45 | (−) 7.1 (−) 15.2 | | | | Yes[20] |
| Polyurethane substrate plasma deposited with 1,1,1-trimethyl-1-pentene coating layer[11] | 31 ± 1 | 0.5 ± 0.3 | 32 ± 1.0 | (−) 27.4 | 100 ± 2.0 | 48 ± 2.0 | 67 ± 1.0 | Yes[20] |
| Polyurethane substrate plasma deposited with PFMCH coating layer.[12] | 19 ± 2.0 | 0.6 ± 0.2 | 20 ± 1.0 | (−) 37.1 | 110 ± 2 | 82 ± 2.0 | 92 ± 2.0 | Yes[20] |

-continued

| | Dispersive Component of Total Surface Energy (mJ/m$^2$) | Polar Component of Total Surface Energy (mJ/m$^2$) | Total Surface Energy (mJ/m$^2$) | Zeta-Potential (mV)[1] | Contact Angle in degrees (H2O) | Contact Angle in degrees (Diiodo-methane) | Contact Angle in degrees (ethylene glycol) | Stable[17] |
|---|---|---|---|---|---|---|---|---|
| Comparative Examples | | | | | | | | |
| VITRO SKIN[13] | 31.55 | 8.52 | 40.07 | | | | | No[16] |
| COFFI film[14] | 28.06 | 9.12 | 37.17 | | | | | No[17] |
| BIOSKIN[15] (Black) | 44.5 | 16.2 | 60.6 | | 46.1 ± 2.6 | 29.4 ± 2.2 | | No[18] |
| BIOSKIN[15] (Brown) | 31.0 | 1.36 | 32.36 | | 89.8 ± 0.3 | 55.7 ± 0.2 | | No[19] |

[1] measured at a pH of about 5.0.
[2] skin from forearm. Measurements may be made as follows: Shave any hair from skin 2-3 days prior to measurement. Place a drop of desired liquid on the skin, which is positioned horizontally. Capture the contact of the drip with a high speed (e.g., at 0.017 seconds per image) video stream for about 3 seconds. Use suitable software to non-spherically trace the droplets and determine the contact angle, e.g., First Ten Angstroms™ Model 200 Dynamic Contact Angle Analyzer. Calculate the mean contact angle for both sides of the drop.
[3] "winter" skin measurement made as described in [2], at a temperature of approximately 0° C., a dew point of approximately −4° C. and a relative humidity of approximately 70%.
[4] "summer" skin measurement made as described in [2], at a temperature of approximately 24° C., a dew point of approximately 18° C. and a relative humidity of approximately 55%.
[5] wet skin measurement made after immersion in distilled water for about 5 min. while still immersed. Solvents used to determine contact angles under water were bromonaphthalene, diiodomethane, and hexane. Contact angles converted into surface energy by Augustine Scientific, Cleveland, OH.
[6] scalp measurements made as described in [2].
[7] lip measurements made as described in [2].
[8] See examples 1 and 2.
[9] Bicomponent polyurethane with plasma-deposited allyl amine coating layer. Plasma deposition performed using pulsed deposition, as described in Example 4, using 25 W continuous wave deposition at 40 kHz power.
[10] Bicomponent polyurethane with plasma-deposited allyl alcohol coating layer. Plasma deposition performed using 7 W continuous wave deposition as described in Example 4.
[11] Bicomponent polyurethane with plasma-deposited 1,1,1-trimethyl-1-pentene coating layer. Plasma deposition performed using continuous wave deposition at 25 W and 40 kHz power.
[12] Bicomponent polyurethane with plasma-deposited PFMCH coating layer. Plasma deposition performed using continuous wave deposition at 25 W and 40 kHz power.
[13] IMS Inc., Orange, CT
[14] distributed by Brechteen, Chesterfield, MI
[15] Beaulax Co., Ltd., Tokyo, Japan
[16] Upon wetting, loss of texture renders substrate unsuitable for re-use as described herein.
[17] Substrate exhibited swelling and loss of texture after one use.
[18] Substrate exhibited loss of texture upon cleaning with solvents such as neat ethanol.
[19] Substrate delaminates, i.e. laminated coating layer is removed, upon rubbing with solvents such as neat ethanol.
[20] Substrate retains texture and coating layer after multiple uses and cleanings, and is stable as defined herein.

Example 5

The following describes one example of using a substrate as described herein to determine deposition of an ingredient (e.g., petrolatum) from a personal care product.[1]

[1] One of skill in the art will understand that a similar method may be used to analyze the deposition of a variety of substances, including active ingredients, perfume raw materials, hydrophilic substances, moisturizers and conditioners, etc.

Consumers typically express a preference for products which moisturize and lubricate the skin, but which do not have a greasy or tacky feel. Depositing the appropriate amount of substances such as petrolatum is related to these desired properties. A hydrophobic substrate having physical properties similar to dry skin as described in Example 4 are used to quantify petrolatum deposition from body wash. Procedure: Wet the surface of a substrate having a surface area of approximately 8 cm×18 cm and a generic shower puff separately under warm running water having a flow rate of from about 2-5 l/min. and a water temperature of from about 35° C.-38° C. for about 5-10 seconds. Dispense approximately 1-5 ml of a rinse-off product onto the substrate surface and spread the rinse-off product onto the surface using a wet finger to ensure sufficiently uniform coverage of the substrate surface. Lightly rub the wetted puff in continuous circular strokes on the substrate surface until a foamy lather is created (about 10 seconds). Allow the lather to remain on the substrate surface for about 15 seconds. Rinse the substrate under running warm water for about 15 seconds. Pat dry with a paper towel, and allow the substrate to air dry at room temperature for about 1-2 minutes. Extract the petrolatum from the substrate surface and analyze by gas chromatography[2].

[2] Extraction and analysis of actives may be performed using any standard analytical technique suitable for the active ingredient, and would be known or developed by one of skill in the art.

One example of a suitable method for extraction and analysis of petrolatum is as follows. Place in a suitable vessel (e.g., a polypropylene centrifuge tube) a representative portion of the substrate to which a rinse-off product has been applied as above, adding a sufficient amount of heptane to immerse the substrate surface. Add an appropriate amount of a suitable internal standard (e.g., squalene). Cap the vessel, shake for several seconds, and vortex for about 30 seconds. Collect the fluid and analyze by gas chromatography. Petrolatum deposition may be quantified by using a multipoint calibration curve constructed from at least five of the most abundant paraffin peaks in a petrolatum standard. Preferably the same type and lot of petrolatum used to formulate the test rinse-off product is used to construct the calibration curve. The paraffin components of petrolatum can be separated on a DB-5HT column (15 m length×0.32 mm diameter, 0.1 μm film thickness) using hydrogen carrier gas with a flow rate of 3.5 mL/min (constant flow) and an appropriate oven temperature program. Detection can be accomplished with a flame ionization detector.

The composition providing a specific level of petrolatum deposition may be subjected to consumer testing. Depending upon the results of the consumer testing, the above protocol may be repeated as needed to selectively identify compositions that provide a more desirable deposition of petrolatum or other desired ingredients.

Example 6

The following describes one example of using a substrate as described herein as part of an apparatus to assess the feel of a substance on hair.

An apparatus designed to simulate the hair rinsing process is connected to an instrument capable of measuring frictional forces (for example, an Instron-type instrument) and containing a load cell of about 1 kg to about 100 kg. The rinsing apparatus comprises: 1) an air-activated clamping device capable of opening and closing to deliver pressures of about 10 psi to about 70 psi to simulate the pressure exerted by hands on hair during rinsing 2) keratinous tissue models as described herein affixed to two opposing sides of the clamping device and 3) one or more spray nozzles capable of delivering water flow rates of from about 50 ml/min. to about 1000 mL/min., for simulating shower conditions. Procedure: Attach the rinsing apparatus to the base of a Stable Micro Systems TA XT Plus™ Texture Analyser equipped with a 5 kg load cell, centering or aligning the clamps perpendicular to the load cell. Set the air pressure to the clamping device to approximately 30 psi. Attach a substrate as described in Example 4 to both faces of the clamp assembly using double-sided foam tape such as Scotch 3M brand double-sided foam tape number 4026. Adjust water flow to spray nozzles to approximately 150 ml/min. Securely attach a sample of human hair (e.g., a hair switch ranging from 2-20 grams weight, from 0.25 to 2.5 inch width, and 4 to 10 inches length) which has been treated with a product to be tested (for example, lathered with shampoo or treated with conditioner) to the load cell clamp of the Instron-type instrument. Supply water to the spray nozzles using a pump. Typical water conditions may include: 0-25 grains/gallon hardness, alternatively 7-10 grains/gallon hardness, and a temperature of about 4° C.-50° C., and alternatively 32° C.-43° C. Close the clamps. Initiate a test sequence which 1) instructs the instrument to raise the load cell to which the hair sample is attached, at a rate of about 10 mm/sec 2) opens the clamps, and 3) instructs the instrument to lower the load cell. Repeat this sequence until the detected frictional force is constant. Alternatively, a predetermined number of sequences may be executed, for example, 20. By calculating the total friction in grams of force (or other suitable unit of force) for rinse friction, products may be ranked relative to each other to assess which products would be expected to have the most pleasant feel.

Example 7

The following example illustrates a method for evaluating adhesion of a transdermal delivery patch to keratinous tissue.

Firmly attach individual substrates as described in Example 3c and 3f-3i to a stable, flat surface, for example, by taping with double-sided tape. Attach a transdermal delivery patch[1] to each substrate by pressing with thumb or finger using a force of about 10 lb. and dragging along the length of the patch 5-10 times, leaving about ½ inch along the length of one side of the delivery patch unadhered to the substrate. Optionally, the substrates with attached patches may be heated to normal body temperature or heated or cooled to another desired temperature. Optionally, the substrates with attached patches may be washed under running warm water emulating a human shower condition then pat dry.

[1] NOVEN placebo patches containing no active ingredient having an acrylic-siliconic polymer adhesives (Manufacturer Noven Pharmaceuticals Inc., Miami, Fla.)

Measure peel force using an Instron tensiometer instrument (Instron 4201, NSTRON, Canton, Mass.). To initiate the test, attach the approximately half inch free end of the patch into the standardized fixture of the Instron upper grip. As the crosshead of the INSTRON is driven upward at a specified speed (about 5-20 inch/min.), the patch is peeled at an approximately 90° angle from the substrate. Monitor the force required to peel the patch by a load weighing system which provides a direct measurement of peel force, expressed as the average load per unit width of the patch. Optionally, peel force may be measured at various time intervals, for example, after 5 min., 1 hour, 12 hours and 24 hours. By correlating the peel force to conditions such as condition of keratinous tissue (e.g., hydrophobic/hydrophilic), conditions of use and shape of body part, adhesives can be developed which more effectively and comfortably adhere to keratenous tissue.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of product evaluation comprising the steps of:
   a) applying a substance to a surface of an artificial substrate to form a substance-coated surface;
      wherein the surface of the artificial substrate has a texture that mimics mammalian keratinous tissue; and
      wherein the surface of the artificial substrate demonstrates at least one physical property selected from the group consisting of: a total surface energy of from about 15 mJ/m$^2$ to about 50 mJ/m$^2$, a polar component of the total surface energy of from about 0 mJ/m$^2$ to about 15 mJ/m$^2$, a zeta-potential at a pH of about 5.0 of from about −30 mV to about 30 mV, and combinations thereof; and
   b) performing at least one analysis of the substance-coated surface.

2. The method according to claim 1, wherein the texture mimics mammalian skin.

3. The method according to claim 1, wherein the texture mimics mammalian hair.

4. The method according to claim 1, wherein the shape of the artificial substrate is substantially planar.

5. The method according to claim 1, wherein the shape of the artificial substrate resembles a mammalian body part.

6. The method according to claim 1, wherein a coating layer comprising at least one coating material is stably affixed to the substrate surface.

7. The method according to claim 6, wherein the coating material is selected from the group consisting of 1,1,1-trimethyl-1-pentene, allyl amine, perfluoromethylcyclohexane, allyl alcohol, and mixtures thereof.

8. The method according to claim 6, wherein the coating layer is textured.

9. The method according to claim 6, wherein the coating layer is hydrophobic, and wherein the substrate surface has a total surface energy of from about 22 mJ/m$^2$ to about 36 mJ/m$^2$, and a polar component of the total surface energy of from about 0 mJ/m$^2$ to about 5 mJ/m$^2$.

10. The method according to claim 6, wherein the coating layer is hydrophilic, and wherein the substrate surface has a total surface energy of from about 35 mJ/m$^2$ to about 45 mJ/m$^2$, and a polar component of the total surface energy of from about 10 mJ/m$^2$ to about 15 mJ/m$^2$.

11. The method according to claim 6, wherein the coating layer is positively charged and wherein the substrate surface has a zeta-potential at a pH of about 5.0 of from about 0 mV to about +30 mV.

12. The method according to claim 6, wherein the coating layer is negatively charged and wherein the substrate surface has a zeta-potential at a pH of about 5.0 of from about −30 mV to about 0 mV.

13. The method according to claim 1, wherein the substance is a consumer product.

14. The method according to claim 1, wherein the substance is a natural substance.

15. The method according to claim 1, wherein the substance is an imitation of a natural substance.

16. A method of consumer product evaluation comprising the steps of:
   a) applying a substance to a surface of a substrate to form a substance-coated surface, wherein:
      i. the substrate is comprised of material selected from the group consisting of polyurethane, polydimethylsiloxane, linear polyethylene, isotactic polypropylene, polystyrene, polyamide, and mixtures thereof;
      ii. the surface of the substrate has a texture that mimics mammalian keratinous tissue;
      iii. a coating layer is stably affixed to the substrate surface, wherein said coating layer comprises a coating material selected from the group consisting of 1,1,1-trimethyl-1-pentene, allyl amine, perfluoromethylcyclohexane, allyl alcohol, and mixtures thereof;
   b) performing at least one analysis of the substance-coated surface to produce a first set of data; and
   c) using the data to aid in product development.

17. The method of claim 16, wherein the substrate is comprised of polyurethane.

18. The method of claim 16, wherein the texture mimics hair.

19. The method of claim 16, wherein the texture mimics mammalian skin.

20. The method of claim 16, wherein the surface of the substrate demonstrates at least one physical property selected from the group consisting of a total surface energy of from about 15 mJ/m$^2$ to about 50 mJ/m$^2$, a polar component of the total surface energy of from about 0 mJ/m$^2$ to about 15 mJ/m$^2$, a zeta-potential at a pH of about 5.0 of from about −30 mV to about 30 mV, and combinations thereof.

21. The method of claim 16, further comprising the steps of applying the substance to living mammalian keratinous tissue and performing at least one analysis of the tissue to produce a second set of data.

22. The method of claim 21, further comprising the step of comparing the first set of data to the second set of data.

23. The method of claim 1, wherein the artificial substrate is comprised of material selected from the group consisting of polyurethane, polydimethylsiloxane, linear polyethylene, isotactic polypropylene, polystyrene, polyamide, and mixtures thereof.

24. The method of claim 23, wherein the artificial substrate is comprised of polyurethane.

25. The method of claim 1, wherein the product is a household cleansing product.

26. The method of claim 1, wherein the analysis includes assessing the retention of the substance on the substance-coated surface.

27. The method of claim 1, wherein the substance includes a perfume raw material.

* * * * *